US006197578B1

(12) United States Patent
Berger et al.

(10) Patent No.: US 6,197,578 B1
(45) Date of Patent: *Mar. 6, 2001

(54) CELLS EXPRESSING BOTH HUMAN CD4 AND A HUMAN FUSION ACCESSORY FACTOR ASSOCIATED WITH HIV INFECTION

(75) Inventors: Edward Berger, Rockville, MD (US); Yu Feng, San Diego, CA (US); Paul Kennedy, Silver Spring; Christopher Broder, Rockville, both of MD (US)

(73) Assignee: The United States of America as represented by the Department of Health and Human Services, Washington, DC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/791,388

(22) Filed: Jan. 30, 1997

Related U.S. Application Data

(60) Provisional application No. 60/010,854, filed on Jan. 30, 1996.

(51) Int. Cl.[7] .......................... C12N 15/00; C12N 15/63; C12N 15/09; C12N 5/00
(52) U.S. Cl. ..................... 435/325; 435/69.1; 435/320.1; 435/455; 435/456
(58) Field of Search ............................. 800/2, 18, 3, 21; 435/172.3, 69.1, 325, 320.1, 455, 456

(56) References Cited

U.S. PATENT DOCUMENTS 5,700,671  12/1997  Prieto et al. ...................... 435/172.3

OTHER PUBLICATIONS

Houdebine, Journal of Biotechnology, vol. 34, pp. 269–287, 1994.*
Wall, Theriogenology, vol. 45, pp. 57–68, 1996.*
Kappel et al., Current Opinion in Biotechnology, vol. 3, pp. 548–553, 1992.*
Strojek & Wagner, Genetic Engineering, vol. 10, pp. 221–246, 1988.*
Cohen, Science, vol. 275, pp. 1261–1264, Feb. 28, 1997.*
Browning et al., Proceedings of the National Academy of Sciences, USA, vol. 94, pp. 14637–14641, Dec. 1997.*
Bieniasz et al., Journal of Virology, vol. 71, pp. 7097–7100, Sep. 1997.*
Picard et al., Virology, vol. 231, pp. 105–111, 1997.*
McKnight et al., Journal of Virology, vol. 71, pp. 1692–1696, Feb. 1997.*
Bradley et al., Biotechnology, vol. 10, pp. 534–539, May 1992.*
Law et al., Journal of Experimental Medicine, vol. 179, pp. 1233–1242, Apr. 1994.*
Jiang and Jolly, J. Hum. Virol., vol. 2, pp. 123–132, Abstract only, 1999.*
Dunn et al., Journal of General Virology, vol. 76, pp. 1327–1336, 1995.*
Snyder et al., Molecular Reproduction and Development, vol. 40, pp. 419–428. (Abstract Only), 1995.*
Loetscher et al., "Cloning of a Human Seven–Transmembrane Domain Receptor, Lestr, That Is Highly Expressed in Leukocytes", *Journal of Biological Chemistry*, vol. 269, No. 1, Jan. 7, 1994, pp. 232–237.
Loretta et al., "Novel sequences expressed by mineralizing human osteoblasts in cultures," *EMBL/GenBank/DDBJ Database*, Accession nr. U16752, Nov. 17, 1994.
Tashiro et al., "Single sequence trap: A cloning strategy for secreted proteins and type I membrane proteins", *Science*, vol. 261, 1993, pp. 600–603.
Nussbaum et al., "Fusogenic mechanisms of enveloped–virus glycoproteins analyzed by a novel recombinant vaccina virus–based assay . . . ", *Journal of Virology*, vol. 68, No. 9, Sep. 1994, pp. 5411–5422.
Feng et al., "HIV–1 entry cofactor: Functional cDNA cloning of a seven–transmembrane. G–protein–coupled receptor", *Science*, vol. 272, May 10, 1996, pp. 872–877.
Oberlin et al., "The CXC chemokine SDF–1 is the ligand for LESTR/fusin and prevents infection by T–Cell–line–adapted HIV–1", *Nature*, vol. 382, Aug. 29, 1996, pp. 833–835.
Cohen, "Likely HIV cofactor found", *Science*, vol. 272, May 10, 1996, pp. 809–810.
Cibelli, et al., Cloned Transgenic Calves Produced from Nonquiescent Fetal Fibroblasts, Science, vol. 280:1256–1258 (May 22, 1998).
Krimpenfort, et al., Generation of Transgenic Dairy Cattle Using 'In Vitro' Embryo Production, Biotechnology vol. 9 (Sep. 1991).

* cited by examiner

*Primary Examiner*—Scott D. Priebe
*Assistant Examiner*—Jill D. Martin
(74) *Attorney, Agent, or Firm*—Needle & Rosenberg, P.C.

(57) ABSTRACT

The susceptibility to human immunodeficiency virus (HIV) infection depends on the cell surface expression of the human CD4 molecule and a human fusion accessory factor associated with HIV infection (CXCR4). CXCR4 is a member of the 7-transmembrane segment superfamily of G-protein-coupled cell surface molecules. CXCR4 plays an essential role in the membrane fusion step of HIV infection. The establishment of stable cell lines that coexpress human CD4 and CXCR4 provides valuable tools for the continuing research of HIV infection and the development of more effective anti-HIV therapeutics.

7 Claims, 2 Drawing Sheets

CELLS EXPRESSING BOTH HUMAN CD4 AND A HUMAN FUSION ACCESSORY FACTOR ASSOCIATED WITH HIV INFECTION This application claims the benefit of provisional application 60/010,854, filed Jan. 30, 1996.

FIELD OF THE INVENTION

The present invention pertains to in vitro and in vivo models for the study of human immunodeficiency virus (HIV) infection and the effectiveness of anti-HIV therapeutics.

The susceptibility to HIV infection depends on the cell surface expression of the human CD4 molecule and a heretofore unidentified human fusion accessory factor. The functional assays described herein identified a molecule, designated CXCR4. The term CXCR4 is preferred, but the terms fusin or HFAF have also been used to refer to the same molecule. Comparison of the nucleotide sequence of the cDNA encoding CXCR4 against a computer database revealed that CXCR4 is a member of the 7-transmembrane segment superfamily of G-protein-coupled cell surface molecules. Many of the superfamily members function as ligand receptors in relation, for example, to peptide hormones, neurotransmitters, and chemokines. CXCR4 has no known ligand, however, and its function is unknown.

A key aspect of the present invention is the discovery that CXCR4 plays an essential role in the membrane fusion step of HIV infection. The establishment of stable, nonhuman cell lines and transgenic mammals having cells that coexpress human CD4 and CXCR4 provides valuable tools for the continuing research of HIV infection and the development of more effective anti-HIV therapeutics. In addition, antibodies against CXCR4, isolated and purified peptide fragments of CXCR4, and CXCR4-binding biologic agents, capable of blocking membrane fusion between HIV and target cells represent potential anti-HIV therapeutics.

BACKGROUND OF THE INVENTION

The HIV infection cycle begins with the entry of the virus into the target cell. The human CD4 molecule is the primary receptor recognized by HIV. The binding of the HIV envelope glycoprotein (env) to the CD4 receptor results in the fusion of virus and cell membranes, which in turn facilitates virus entry into the host. The eventual expression of env on the surface of the HIV-infected host cell enables this cell to fuse with uninfected, CD4-positive cells, thereby spreading the virus.

Recent studies have shown that this HIV fusion process occurs with a wide range of human cell types that either express human CD4 endogenously or have been engineered to express human CD4. The fusion process, however, does not occur with nonhuman cell types engineered to express human CD4. Although such nonhuman cells can still bind env, membrane fusion does not follow. The disparity between human and nonhuman cell types exists apparently because membrane fusion requires the coexpression of human CD4 and an accessory factor specific to human cell types. Because they lack this accessory factor, nonhuman cell types engineered to express only human CD4 are incapable of membrane fusion, and are thus nonpermissive for HIV infection. To date there has been no report of any stable, nonhuman cell line that is permissive for HIV infection as a result of human CD4 and CXCR4 coexpression.

The importance of human CD4 and CXCR4 coexpression also impacts the establishment of a successful small animal model. The development of a small animal model is crucial to the study of HIV infection and the effectiveness of anti-HIV therapeutics. In recent years, researchers have bred transgenic animals having cells that express human CD4. See, for example, Dunn et al., *Human immunodeficiency virus type 1 infection of human CD4-transgenic rabbits*, J. Gen. Vir. 76:1327–1336 (1995); Snyder et al., *Development and Tissue-Specific Expression of Human CD4 in Transgenic Rabbits*, Mol. Reprod. & Devel. 40:419–428 (1995); Killeen et al., *Regulated Expression of Human CD$ Rescues Helper T-Cell Development in Mice Lacking Expression of Endogenous CD4*, EMBRO J. 12:1547–1553 (1993); Forte et al., *Human CD4 Produced in Lymphoid Cells of Transgenic Mice Binds HIV p120 and Modifies the Subsets of Mouse T-Cell Populations*, Immunogenetics 38:455–459 (1993). These animals, however, have low susceptibility to HIV infection, presumably because of the lack of CXCR4 expression. To date, there has been no report of any transgenic animal that is significantly susceptible to HIV infection as a result of human CD4 and CXCR4 coexpression.

Without an effective vaccine, the number of individuals infected with HIV will likely increase substantially. Furthermore, in the absence of effective therapy, most individuals infected with HIV will develop acquired immune deficiency syndrome (AIDS) and succumb to either opportunistic infections and malignancies that result from the deterioration of the immune system, or the direct pathogenic effects of the virus. Despite the present availability of some anti-HIV agents that slow disease progression, a pressing need remains for more effective therapeutics and drug combinations. To date, there has been no report of any anti-HIV therapeutic that relates to CXCR4.

It is apparent from the foregoing that a need exists for in vitro and in vivo models suitable to the study of HIV infection and the effectiveness of anti-HIV therapeutics. By the same token, the need remains for more effective anti-HIV therapeutics. Although CXCR4 is a member of the known 7-transmembrane segment superfamily of G-protein-coupled cell surface molecules, the essential role of CXCR4 in the membrane fusion step of HIV infection was not elucidated heretofore.

SUMMARY OF THE INVENTION

Accordingly, it is an objective of the present invention is the establishment of stable, nonhuman cell lines, the cells of which contain DNA encoding CXCR4 and express both human CD4 and CXCR4.

Another objective of the present invention is the establishment of transgenic mammals having cells that coexpress human CD4 and CXCR4.

A further objective of the present invention is the production of antibodies, preferably monoclonal antibodies, against CXCR4 that block membrane fusion between HIV and a target cell or between an HIV infected cell and an uninfected CD4 positive cell.

Yet another objective is the isolation and purification of peptide fragments of CXCR4 that block membrane fusion between HIV and a target cell. Also included are fragments of HIV env polypeptide that block membrane fusion between HIV and target cell or between an HIV infected cell and an uninfected CD4 positive cell.

It also is an objective of the present invention to isolate and purify CXCR4-binding agents, both biologic and chemical compounds, that block membrane fusion between HIV and a target cell or between an HIV infected cell and an uninfected CD4 positive cell. A biologic agent of the invention includes stromal cell derived factor 1 (SDF-1), which is a natural ligand for CXCR4.

In accomplishing these and other objectives, there is provided a stable, nonhuman cell line, the cells of which contain DNA encoding a human accessory fusion factor associated with HIV infection (CXCR4), and coexpress human CD4 and CXCR4; a transgenic non-human mammal comprised of cells that coexpress human CD4 and CXCR4; an antibody against CXCR4 that blocks membrane fusion between HIV and a target cell; a monoclonal antibody against CXCR4 that blocks membrane fusion between HIV and a target cell; an isolated and purified peptide fragment of CXCR4, wherein said peptide fragment blocks membrane fusion between HIV and a target cell; and an isolated and purified CXCR4-binding biologic agent, wherein said biologic agent blocks membrane fusion between HIV and a target cell.

Also included in the invention are methods of treating a subject having or at risk of having an HIV-related disorder associated with expression of CXCR4 comprising administering to an HIV infected or susceptible cell of the subject, a reagent that suppresses CXCR4. Therapeutic methods of the invention using an anti-CXCR4 antibody are described. Further, the invention also includes methods of gene therapy wherein an antisense nucleic acid that hybridizes to a CXCR4 nucleic acid is administered to a subject. The reagent is introduced into the cell using a carrier, such as a vector. Administration of the reagent can be in vivo or ex vivo.

In another embodiment, the invention provides a method for detecting susceptibility of a cell to HIV infection by detecting fusion of a test cell with a cell that expresses HIV-env. Also included are methods of identifying compositions which either bind to CXCR4 or block membrane fusion between HIV and a target cell or between an HIV-infected cell and a CXCR4 positive uninfected cell. Preferably the CXCR4 cell is also CD4 positive.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Figure 1:
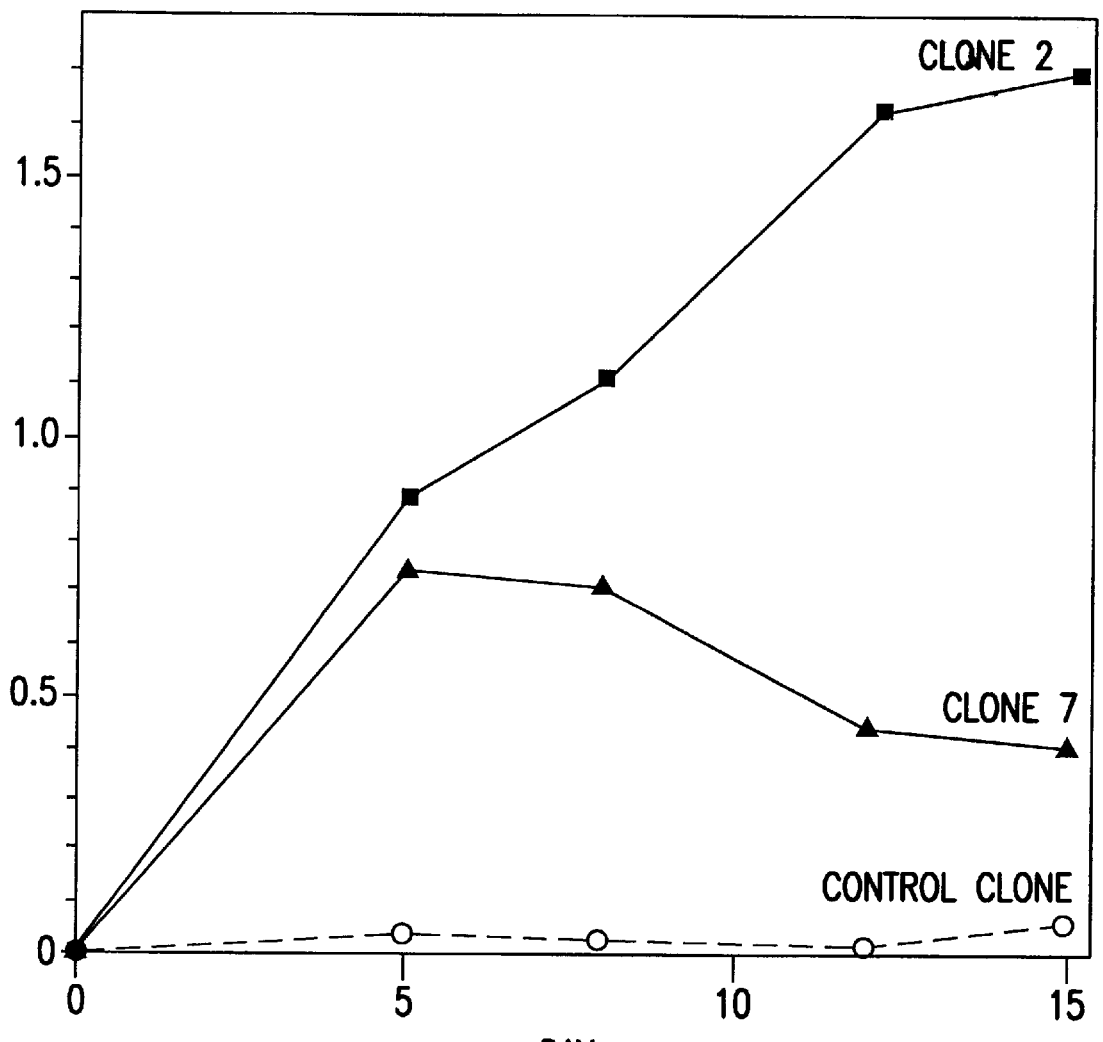
FIG. 1 depicts the susceptibility to HIV-1 infection (as measured by p24 production) of stable transformed mink cell lines coexpressing human CD4 and CXCR4 (clones 2 and 7) in contrast to stable transformed mink cell lines coexpressing human CD4 and lacZ (negative control clone).

In accordance with the present invention, the phrase "human fusion accessory factor associated with HIV infection" (CXCR4) refers to a cellular protein of the 7-transmembrane segment superfamily of G-protein-coupled cell surface molecules that is associated with the fusion of virus and target cell membranes in HIV infection. The essential role of CXCR4 in the membrane fusion step of HIV infection was determined by functional assay of the effects of recombinant CXCR4 (i.e., assay by vaccinia cell fusion system or HIV infection), and was confirmed by antibody inhibition assay.

ISOLATION OF cDNA ENCODING CXCR4

A human cDNA plasmid library prepared from HeLa cells can be obtained, for example, from Invitrogen (San Diego, Calif.). In this library, the cDNAs are cloned directionally into a plasmid vector (pcDNA3) under the transcriptional control of a bacteriophage T7 promoter. Murine NIH/3T3 cells (nonpermissive for HIV-1 fusion) are cotransfected with the library cDNA and plasmid pTF7-3 (Fuerst et al., Proc. Nat'l Acad. Sci USA 83:8122–8126 (1986)), which contains the T7 RNA polymerase gene under the transcriptional control of a vaccinia promoter. As a negative control, NIH/3T3 cells are cotransfected with a single random cDNA from the library and pTF7-3. The cells are then infected with vaccinia virus recombinant vCB-3 (Broder et al., Virol. 193:483–491 (1993)), which contains the human CD4 gene under the transcriptional control of a vaccinia promoter.

A separate population of NIH/3T3 cells is coinfected with vaccinia viruses vSC-60 (Broder & Berger, Proc. Nat'l Acad. Sci. USA 92:9004–9008 (1995)), which contains the HIV-1 env gene (IIIB isolate) under the transcriptional control of a vaccinia promoter, and vCB-21R (Alkhatib et al., J Virol. 70:5487, 1996 ), which contains the Escherichia coli lacZ gene under the transcriptional control of a T7 promoter ($P_{T7}$-lacZ). As a negative control, another population of NIH/3T3 cells is coinfected with vCB-21R and vCB-16 (Broder & Berger, supra), which contains a mutant env gene encoding an uncleavable, nonfusogenic unc/env. The cell populations are incubated overnight at 31° C. to allow expression of the vaccinia-encoded proteins. The CD4-positive cells containing library cDNA and pTF7-3 are mixed with env-positive cells containing $P_{T7}$-lacZ, and incubated for 3 hours at 37° C. to allow fusion. The cultures are then stained for β-galactosidase in situ with X-gal. The number of blue cells are scored.

In respective fusions with env-positive cells, a much greater number of blue cells was observed with CD4-positive cells containing library cDNA than with the negative control, CD4-positive cells containing a single random cDNA from the library. In addition, in respective fusions with unc/env-positive cells, low background numbers of blue cells were observed with CD4-positive cells containing library cDNA. These data suggested that the library contained a cDNA encoding a product, CXCR4, capable of rendering CD4-positive murine cells permissive for env-mediated fusion.

To isolate a single cDNA plasmid encoding CXCR4, the library is subdivided into approximately 1000 tubes each containing about 4000 transformed bacterial cells. Plasmid DNA is prepared initially from pools of 10 tubes. Each batch is cotransfected with pTF7-3 in murine NIH/3T3 cells, and assayed for the presence of β-galactosidase after fusion with env-positive cells containing $P_{T7}$-lacZ as described above. Individual tubes from positive batches are then screened. Positive tubes are then subdivided into approximately 1000 tubes each containing about 4 transformed bacterial cells. Plasmid DNA is prepared individually from these tubes and then screened similarly. The contents of a positive tube are plated onto agar plates. Individual colonies are picked and grown for plasmid preparation. Using this method, a single cDNA plasmid clone, $pP_{T7}$-CXCR4, is obtained that could render CD4-positive murine cells permissive for env-mediated fusion.

Nucleotide sequence analysis revealed that the cDNA insert of $pP_{T7}$-CXCR4 had an open reading frame encodeing a protein, CXCR4. A computer database search revealed that the cDNA of $pP_{T7}$-CXCR4 had been previously reported as corresponding to a protein of the 7-transmembrane segment superfamily of human G-protein-coupled cell surface molecules. See Herzog et al, *DNA Cell Biol.* 12:465–71 (1993); Federspiel et al., *Genomics* 16:707–12 (1993); Jazin et al., *Regul. Pept.* 47:247–58 (1993); Nomura et al., *Int. Immunol* 5:1239–49 (1993); Loetscher et al., *J. Biol Chem.* 269:232–37 (1994). The CXCR4 of the present invention includes the sequence as in Loetscher, et al., *supra,* with the exception that the Loetscher sequence has eight consecutive T residues beginning at nucleotide 1076 and CXCR4 has seven. (Feng, et al., *Science* 272:872, 1996). All of these references are hereby incorporated herein by reference in their entirety.

The cDNA of $pP_{T7}$-CXCR4 is cloned into the multiple cloning site of pSC59, which contains a strong vaccinia promoter flanked by sequences of the vaccinia virus thymidine kinase gene. The resulting plasmid $pP_{vac}$-CXCR4 is used to generate vaccinia recombinant vCXCR4, which permits high level expression of CXCR4 upon infection of various cell types.

CXCR4 FUNCTIONAL ASSAY

In a first embodiment, the invention provides a method for detecting susceptibility of a cell to HIV infection. The method includes incubating a first cell to be tested for susceptibility, with a second cell which is known to express HIV-env, under suitable conditions to allow fusion of the two cells (see below for an example of suitable conditions). Susceptibility is indicated by detecting fusion of the cells. Detection is preferably by a reporter gene, as described below for lacZ, however, other reporter means are known in the art and are discussed in the present specification under "Screen For CXCR4 Blocking Agents".

Table 1 provides the results of a vaccinia cell fusion system to assay the functional ability of CXCR4 to confer env-mediated fusion competence to CD4-positive nonhuman cells. Murine NIH/3T3 cells or human HeLa cells are coinfected with various vaccinia viruses: vTF7-3 (containing the T7 RNA polymerase gene); vCB3 (containing the human CD4 gene); vCXCR4 (containing the CXCR4 gene); and vaccinia WR (a negative control). A different cell population is coinfected with various vaccinia viruses: vCB-21R (containing the *E coli* lacZ gene under the transcriptional control of a T7 promoter ($P_{T7}$-lacZ) along with either vSC60 (containing the HIV-1 env gene (WB isolate)) or vCB-16 (a negative control, containing a mutant env gene encoding an uncleavable, nonfusogenic unc/env). The cell populations are incubated overnight at 31° C. to allow expression of the vaccinia-encoded proteins. The cells are washed and mixtures are prepared in 96-well microtiter plates. Each well contains equal numbers of the indicated pairs of T7 RNA polymerase-containing cells and lacZ gene-containing cells. Replicate plates are incubated for 4 hours at 37° C. to allow fusion. Samples on one plate are treated with NP-40 and aliquots are assayed for β-galactosidase activity using a 96-well absorbance reader. Samples on the second plate are stained with crystal violet for syncytia analysis by light microscopy.

The β-galactosidase and syncytia data indicate that NIH/3T3 cells coexpressing human CD4 and CXCR4 were highly competent for fusion with cells expressing wildtype env. In contrast, the data clearly indicate that NIH/3T3 cells coexpressing human CD4 alone or CXCR4 alone were incompetent for fusion with cells expressing wild-type env. Furthermore, the background levels of β-galactosidase production and the absence of syncytia formation indicated that NIH/3T3 cells coexpressing human CD4 and CXCR4 did not fuse with cells expressing mutant unc/env.

Table 2 provides the results of a vaccinia cell fusion system to assay the functional ability of CXCR4 to confer env-mediated fusion competence to a range diverse CD4-positive nonhuman cell types: NIH/3T3 (murine); BS-C-1 (African green monkey); and Mv 1 Lu (mink). In addition, unusual, fusion-incompetent, CD4-positive human cell types are tested (U-87 MG glioblastoma; and SCL1).

Several colonies of stable, transformed mink cells that coexpressed human CD4 and CXCR4 are tested for susceptibility to HIV-1 infection. Transformants containg the human CD4 gene and the lacZ gene are used as negative controls. Direct measurements of p24 (HIV core antigen) production indicate that HIV-1 infection was productive with cells that coexpressed human CD4 and CXCR4, but not with the negative controls (FIG. 1). Moreover, the efficiency of HIV-1 infection of transformed, CD4-positive, CXCR4-positive, nonhuman cells is high enough to be detected directly without cocultivation with human CD4-positive target cells.

Preferably, in the fusion method of the invention, the first or the second cell contains a reporter means and at least the test cell, or first cell, is a T cell. A first or second cell includes typically includes a T-cell for in vivo use and NIH-3T3 cells or any of the cells described in the following section for use in vitro. The fusion method described herein is also particularly useful for screening fusion inhibiting agents and pharmacological agents useful in treatment of HIV infection, both prophylactically and after infection. Examples of these agents are described in more detail below, and include but are not limited to peptides, antibodies, peptidomimetics, and chemical compounds.

Cell Lines

In one embodiment, the present invention provides human and nonhuman cell lines, the cells of which contain DNA encoding CXCR4 and coexpress human CD4 and CXCR4. The cells which provide the starting material in which CXCR4 are expressed must be CXCR4 negative, but can be either CD4 positive or CD4 negative cells. Suitable cell types include but are not limited to, cells of the following types: NIH-3T3 murine fibroblasts, quail QT6 quail cells, canine Cf2Th thymocytes, MV1 Lu mink lung cells, Sf9 insect cells, primary T-cells, and human T-cell lines such as H9, U-87 MG glioma cell, SCL1 squamous cell carcinoma cells (negative for both CXCR4 and CD4) and CEM. Such cells are described, for example, in the Cell Line Catalog of the American Type Culture Collection (ATCC, Rockville, Md., USA, 20852). The stable transfer of genes into mammalian cells has been well described in the art. See, for example, Ausubel et al., *Introduction of DNA Into Mammalian Cells,* in CURRENT PROTOCOLS IN MOLECULAR BIOLOGY, sections 9.5.1–9.5.6 (John Wiley & Sons, Inc. 1995).

CXCR4 can be expressed using inducible or constituitive regulatory elements for such expression. Commonly used constituitive or inducible promoters, for example, are known in the art. The desired protein encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the desired molecule may occur through the transient expression of the introduced sequence. Alternatively, permanent expression may occur through the integration of the introduced sequence into the host chromosome. Therefore the cells can be transformed stably or transiently.

An example of a vector that may be employed is one which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors include vaccinia virus expression vectors. A third class of vectors relies upon the integration of the desired gene sequences into the host chromosome. Cells which have stably integrated the introduced DNA into their chromosomes may be selected by also introducing one or more markers (e.g., an exogenous gene) which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., Mol. Cell. Biol., 3:280 (1983), and others.

Once the vector or DNA sequence containing the construct has been prepared for expression, the DNA construct may be introduced (transformed) into an appropriate host. Various techniques may be employed, such as protoplast fusion, calcium phosphate precipitation, electroporation or other conventional techniques.

TRANSGENIC ANIMALS

In another embodiment, the present invention relates to transgenic non-human animals having cells that coexpress human CD4 and CXCR4. Such transgenic animals represent a model system for the study of HIV infection and the development of more effective anti-HIV therapeutics. The transgenic animals of the invention can be produced from animals which express CD4 or from animals that do not express CD4. However, while the invention provides transgenic animals that express CXCR4 alone, the preferred invention transgenic non-human animal co-expresses CD4 and CXCR4. The invention also envisions transgenic animals that express other co-factors necessary for HIV-env-mediated cell fusion.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

It is highly preferred that the transgenic animals of the present invention be produced by introducing into single cell embryos DNA encoding CXCR4 and DNA encoding human CD4, in a manner such that these polynucleotides are stably integrated into the DNA of germ line cells of the mature animal and inherited in normal mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. For instance, reviews of standard laboratory procedures for microinjection of heterologous DNAs into mammalian (mouse, pig, rabbit, sheep, goat, cow) fertilized ova include: Hogan et al., MANIPULATING THE MOUSE EMBRYO (Cold Spring Harbor Press 1986); Krimpenfort et al., *Bio/Technology* 9:86 (1991); Palmiter et al., *Cell* 41:343 (1985); Kraemer et al., GENETIC MANIPULATION OF THE EARLY MAMMALIAN EMBRYO (Cold Spring Harbor Laboratory Press 1985); Hammer et al., *Nature,* 315:680 (1985); Purcel et al., *Science,* 244:1281 (1986); Wagner et al., U.S. Pat. No. 5,175,385; Krimpenfort et al., U.S. Pat. No. 5,175,384, the respective contents of which are incorporated by reference. The cDNA encoding CXCR4 can be fused in proper reading frame under the transcriptional and translational control of a vector to produce a genetic construct that is then amplified, for example, by preparation in a bacterial vector, according to conventional methods. See, for example, the standard work: Sambrook et al., MOLECULAR CLONING: A LABORATORY MANUAL (Cold Spring Harbor Press 1989), the contents of which are incorporated by reference. The amplified construct is thereafter excised from the vector and purified for use in producing transgenic animals.

Production of transgenic animals containing the gene for human CD4 have been described. See Snyder et al., supra; Dunn et al., supra, the contents of which therefore are incorporated by reference.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a DNA sequence comprising a modified CXCR4 coding sequence. In a preferred embodiment, the CXCR4 gene is disrupted by homologous targeting in embryonic stem cells. For example, the entire mature C-terminal region of the CXCR4 gene may be deleted as described in the examples below. Optionally, the CXCR4 disruption or deletion may be accompanied by insertion of or replacement with other DNA sequences, such as a non-functional CXCR4 sequence. In other embodiments, the transgene comprises DNA antisense to the coding sequence for CXCR4. In another embodiment, the transgene comprises DNA encoding an antibody or receptor peptide sequence which is able to bind to CXCR4. Where appropriate, DNA sequences that encode proteins having CXCR4 activity but differ in nucleic acid sequence due to the degeneracy of the genetic code may also be used herein, as may truncated forms, allelic variants and interspecies homologues.

ANTIBODIES AGAINST CXCR4 INHIBIT FUSION

In another embodiment, the present invention provides to antibodies against CXCR4 that block env-mediated membrane fusion (i) associated with HIV entry into a human CD4-positive target cell or (ii) between an HIV-infected cell and an uninfected human CD4-positive target cell. Such antibodies are useful as research and diagnostic tools in the study of HIV infection and the development of more effective anti-HIV therapeutics. In addition, pharmaceutical compositions comprising antibodies against CXCR4 may represent effective anti-HIV therapeutics.

A target cell includes typically includes a T-cell for in vivo use and NIH-3T3 cells or any of the above-listed cells for use in vitro. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., *Production of Polyclonal Antisera,* in IMMUNOCHEMICAL PROTOCOLS (Manson, ed.), pages 1–5 (Humana Press 1992); Coligan et al., *Production of Polyclonal Antisera in Rabbits, Rats, Mice and Hamsters,* in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, CXCR4 the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G (IgG),* in METHODS IN MOLECULAR BIOLOGY, VOL. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications are conceivable for the antibodies of the present invention. For example, antibodies of the present invention may also be derived from subhuman primate antibody. General techniques for raising therapeutically useful antibodies in baboons may be found, for example, in Goldenberg et al., International Patent Publication WO 91/11465 (1991) and Losman et al., *Int. J. Cancer* 46:310 (1990), which are hereby incorporated by reference.

Alternatively, a therapeutically useful anti-CXCR4 antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989), which is hereby incorporated in its entirety by reference. Techniques for producing humanized monoclonal antibodies are described, for example, by Jones et al., *Nature* 321:522 (1986); Riechmann et al., *Nature* 332:323 (1988); Verhoeyen et al., *Science* 239: 1534 (1988); Carter et al., *Proc. Nat'l Acad. Sci. USA* 89: 4285 (1992); Sandhu, *Crit. Rev. Biotech.* 12: 437 (1992); and Singer et al., *J. Immunol.* 150: 2844 (1993), which are hereby incorporated by reference.

Antibodies of the invention also may be derived from human antibody fragments isolated from a combinatorial immnunoglobulin library. See, for example, Barbas et al., METHODS: A COMPANION TO METHODS IN ENZYMOLOGY, VOL. 2, page 119 (1991); Winter et al., *Ann. Rev. Immunol.* 12:433 (1994), which are hereby incorporated by reference. Cloning and expression vectors that are useful for producing a human immnunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5 S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, e.g., Sandhu, *supra*. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., *Science* 242:423–426 (1988); Ladner et al., U.S. Pat. No. 4,946,778; Pack et al., *Bio/Technology* 11:1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

It is also envisioned that antibodies included in the invention may block HIV-env mediated cell fiusion or infection by blocking the interaction between CD4, CXCR4 and HIV, without actually "binding" to CXCR4. Therefore, all of the above descriptions regarding antibodies that bind to CXCR4 also apply to antibodies that block HIV-env mediated infection or fusion.

PEPTIDE FRAGMENTS OF CXCR4

In another embodiment, the present invention relates to substantially purified peptide fragments of CXCR4 that block membrane fusion between HIV and a target cell or cell fusion between an HIV-infected cell and a susceptible uninfected cell. A "susceptible" uninfected cell should express both CD4 and CXCR4. Such peptide fragments could represent research and diagnostic tools in the study of HIV infection and the development of more effective anti-HIV therapeutics. In addition, phannaceutical compositions comprising isolated and purified peptide fragments of CXCR4 may represent effective anti-HIV therapeutics.

It is also envisioned that a peptide fragment useful for blocking membrane fusion as described herein, includes fragments of HIV env.

The term "substantially purified" as used herein refers to a molecule, such as a peptide that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify CXCR4 peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

The invention relates not only to fragments of naturally-occurring CXCR4, but also to CXCR4 mutants and chemically synthesized derivatives of CXCR4 that block membrane fusion between HIV and a target cell.

For example, changes in the amino acid sequence of CXCR4 are contemplated in the present invention. CXCR4 can be altered by changing the DNA encoding the protein. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, other variants and fragments of CXCR4 can be used in the present invention. Variants include analogs, homologs, derivatives, muteins and mimetics of CXCR4 that retain the ability to block membrane fusion. Fragments of the CXCR4 refer to portions of the amino acid sequence of CXCR4 that also retain this ability. The variants and fragments can be generated directly from CXCR4 itself by chemical modification, by proteolytic enzyme digestion, or by combinations thereof. Additionally, genetic engineering techniques, as well as methods of synthesizing polypeptides directly from amino acid residues, can be employed.

Non-peptide compounds that mimic the binding and function of CXCR4 ("mimetics") can be produced by the approach outlined in Saragovi et al., Science 253: 792–95 (1991). Mimetics are molecules which mimic elements of protein secondary structure. See, for example, Johnson et al., "Peptide Turn Mimetics," in BIOTECHNOLOGY AND PHARMACY, Pezzuto et al., Eds., (Chapman and Hall, New York 1993). The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of CXCR4 itself.

Variants and fragments also can be created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit., and CURRENT PROTOCOLS IN MOLECULAR BIOLOGY, vols. 1 & 2, supra.

If the compounds described above are employed, the skilled artisan can routinely insure that such compounds are amenable for use with the present invention utilizing cell fusion assays known in the art, or for example, the exemplary vaccinia cell fusion system described herein. If a compound blocks env-mediated membrane fusion (I) involved in HIV entry into a human CD4-positive target cell or (ii) between an HIV-infected cell and an uninfected human CD4-positive target cell, the compounds are suitable according to the invention. The preferred peptide fragments of CXCR4 according to the invention include those which correspond to the regions of CXCR4 that are exposed on the cell surface.

CXCR4-BINDING AND BLOCKING AGENTS

In yet another embodiment, the present invention relates to substantially purified CXCR4-binding and/or blocking agents that block membrane fusion between HIV and a target cell. Such agents could represent research and diagnostic tools in the study of HIV infection and the development of more effective anti-HIV therapeutics. In addition, pharmaceutical compositions comprising isolated and purified CXCR4-binding agents may represent effective anti-HIV therapeutics. The phrase "CXCR4-binding agent" denotes the natural ligand of CXCR4, a synthetic ligand of CXCR4, or appropriate fragments of the natural or synthetic ligands which either bind to CXCR4 or block CXCR4 in HIV-env mediated membrane fusion. The term includes both biologic agents and chemical compounds. The determination and isolation of ligand/compositions is well described in the art. See, e.g., Lerner, Trends NeuroSci. 17:142–146 (1994), which is hereby incorporated in its entirety by reference.

Various chemokines may function as a biologic agent as a ligand for CXCR4. For example, stromal cell derived factor-1 (SDF-1) is a ligand for CXCR4 and is included as a biologic agent of the invention. Derivatives, analogs, mutants and CXCR4 binding fragments of SDF-1 are useful for blocking env-mediated membrane fusion.

An CXCR4-binding agent that blocks env-mediated membrane fusion (I) involved in HIV entry into a human CD4-positive target cell or (ii) between an HIV-infected cell and an uninfected human CD4-positive target cell, is suitable according to the invention.

SCREEN FOR CXCR4 BINDING AND BLOCKING COMPOSITIONS

In another embodiment, the invention provides a method for identifying a composition which binds to CXCR4 or blocks HIV env-mediated membrane fusion. The method includes incubating components comprising the composition and CXCR4 under conditions sufficient to allow the components to interact and measuring the binding of the composition to CXCR4. Compositions that bind to CXCR4 include peptides, peptidomimetics, polypeptides, chemical compounds and biologic agents as described above.

Incubating includes conditions which allow contact between the test composition and CXCR4. Contacting includes in solution and in solid phase. The test ligand(s)/composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs)

(Landegren, et al., *Science*, 241:1077, 1988), and the like. Molecular techniques for DNA analysis have been reviewed (Landegren, et al., *Science*, 242:229–237, 1988).

Any of a variety of procedures may be used to clone the genes of the present invention when the test composition is in a combinatorial library or is expressed as a gene product (as opposed to a chemical composition). One such method entails analyzing a shuttle vector library of DNA inserts (derived from a cell which expresses the composition) for the presence of an insert which contains the composition gene. Such an analysis may be conducted by transfecting cells with the vector and then assaying for expression of the composition binding activity. The preferred method for cloning these genes entails determining the amino acid sequence of the composition protein. Usually this task will be accomplished by purifying the desired composition protein and analyzing it with automated sequencers. Alternatively, each protein may be fragmented as with cyanogen bromide, or with proteases such as papain, chymottypsin or trypsin (Oike, Y., et al., *J. Biol. Chem.*, 257:9751–9758 (1982); Liu, C., et al., *Int. J. Pept. Protein Res.*, 21:209–215 (1983)). Although it is possible to determine the entire amino acid sequence of these proteins, it is preferable to determine the sequence of peptide fragments of these molecules.

To determine if a composition can functionally complex with the receptor protein, induction of the exogenous gene is monitored by monitoring changes in the protein levels of the protein encoded for by the exogenous gene, for example. When a composition(s) is found that can induce transcription of the exogenous gene, it is concluded that this composition(s) can bind to the receptor protein coded for by the nucleic acid encoding the initial sample test composition (s).

Expression of the exogenous gene can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol acetyltransferase gene, an alkaline phosphatase gene, beta-galactosidase, a luciferase gene, a green fluorescent protein gene, guanine xanthine phosphoribosyltransferase, alkaline phosphatase, and antibiotic resistance genes (e.g., neomycin phosphotransferase).

Expression of the exogenous gene is indicative of composition-receptor binding, thus, the binding or blocking composition can be identified and isolated. The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that bind to CXCR4. Ligands/compositions that bind to CXCR4 can be assayed in standard cell:cell fusion assays, such as the vaccinia assay described herein to determine whether the composition inhibits or blocks env-mediated membrane fusion (i) involved in HIV entry into a human CD4-positive target cell or (ii) between an HIV-infected cell and an uninfected human CD4-positive target cell.

PHARMACEUTICAL COMPOSITIONS

The invention also contemplates various pharmaceutical compositions that block membrane fusion between HIV and a target cell. The pharmaceutical compositions according to the invention are prepared by bringing an antibody against CXCR4, an isolated and purified peptide fragment of CXCR4, or an isolated and purified CXCR4-binding biologic agent according to the present invention into a form suitable for administration (e.g., a pharmaceutically acceptable carrier) to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co., 1405–1412, 1461–1487 (1975) and *The National Formulary XIV.*, 14th ed. Washington: American Pharmaceutical Association (1975), the contents of which are hereby incorporated by reference. The pH and exact concentration of the various components of the pharmaceutical composition are adjusted according to routine skills in the art. See *Goodman and Gilman's The Pharmacological Basis for Therapeutics* (7th ed.).

In another embodiment, the invention relates to a method of blocking the membrane fusion between HIV and a target cell. This method involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The dosage should not be so large as to cause adverse side effects, such as unwanted cross-reactions, anaphylactic reactions and the like. Generally, the dosage will vary with the age, condition, sex, and extent of the disease in the patient and can be determined by one skilled in the art. The dosage can be adjusted by the individual physician in the event of any contraindications and can be readily ascertained without resort to undue experimentation. In any event, the effectiveness of treatment can be determined by monitoring the level of CD4+ T-cells in a patient. An increase or stabilization in the relative number of CD4+ cells should correlate with recovery of the patient's immune system.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science,* 249: 1527–1533 (1990), which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) GOODMAN AND GILMAN'S: THE PHARMACOLOGICAL BASES OF THERAPEUTICS, 8th ed., Pergamon Press; and REMINGTON'S PHARMACEUTICAL SCIENCES, 17th ed. (1990), Mack Publishing Co., Easton, Pa., each of which is herein incorporated by reference. Effectiveness of the dosage can be monitored by CD4+ count as described above in this section.

The pharmaceutical compositions of the invention, including antibodies, peptides, peptidomimetics, chemical compositions, etc., are all useful for treating subjects either having or at risk of having an HIV related disorder. AIDS and ARC are preferred examples of such disorders. HIV-associated disorders have been recognized primarily in "at risk" groups, including homosexually active males, intravenous drug users, recipients of blood or blood products, and certain populations from Central Africa and the Caribbean. The syndrome has also been recognized in heterosexual partners of individuals in all "at risk" groups and in infants of affected mothers.

The immunotherapeutic method of the invention includes a prophylactic method directed to those hosts at risk for the HIV infection. For example, the method is useful for humans at risk for HIV infection. A "prophylactically effective" amount of antibody or peptide, for example, refers to that amount which is capable of blocking env-mediated membrane fusion in HIV entry into a human CD4-positive target cell or between an HIV-infected cell and an uninfected human CD4-positive target cell.

Transmission of HIV occurs by at least three known routes: sexual contact, blood (or blood product) transfusion and via the placenta. Infection via blood includes transmission among intravenous drug users. Since contact with HIV does not necessarily result in symptomatic infection, as determined by seroconversion, all humans may be potentially at risk and, therefore, should be considered for prophylactic treatment by the therapeutic method of the invention.

The compositions described herein and useful in the method of the invention can be administered to a patient prior to infection with HIV (ie., prophylactically) or at any of the stages described below, after initial infection. The HIV infection may run any of the following courses: 1) approximately 15% of infected individuals have an acute illness, characterized by fever, rash, and enlarged lymph nodes and meningitis within six weeks of contact with HIV. Following this acute infection, these individuals become asymptomatic. 2) The remaining individuals with HIV infection are not symptomatic for years. 3) Some individuals develop persistent generalized lymphadenopathy (PGL), characterized by swollen lymph nodes in the neck, groin and axilla. Five to ten percent of individuals with PGL revert to an asymptomatic state. 4) Any of these individuals may develop AIDS-related complex (ARC); patients with ARC do not revert to an asymptomatic state. 5) Individuals with ARC and PGL, as well as asymptomatic individuals, eventually (months to years later) develop AIDS which inexorably leads to death.

GENE THERAPY

In yet another embodiment, the invention provides a method of treating a subject having or at risk of having an HIV-related disorder associated with expression of CXCR4 comprising administering to an HIV infected or susceptible cell of the subject, a reagent that suppresses CXCR4. Therapeutic methods of the invention using an anti-CXCR4 antibody have been described above. The invention also includes methods of gene therapy wherein an antisense nucleic acid that hybridizes to a CXCR4 nucleic acid is administered to a subject. The reagent is introduced into the cell using a carrier, such as a vector. Administration of the reagent can be in vivo or ex vivo.

This approach employs, for example, antisense nucleic acids (i.e., nucleic acids that are complementary to, or capable of hybridizing with, a target nucleic acid, e.g., a nucleic acid encoding a CXCR4 polypeptide), ribozymes, or triplex agents. The antisense and triplex approaches function by masking the nucleic acid, while the ribozyme strategy functions by cleaving the nucleic acid. In addition, antibodies that bind to CXCR4 polypeptides can be used in methods to block the entry of HIV into a cell or block cell fusion between HIV infected and uninfected cells.

The use of antisense methods to inhibit the in vitro translation of genes is well known in the art (see, e.g., Marcus-Sakura, *Anal. Biochem.,* 172:289, 1988). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (see, e.g., Weintraub, *Scientific American,* 262:40, 1990). The antisense nucleic acids hybridize to corresponding nucleic acids, such as mRNAs, to form a double-stranded molecule, which interferes with translation of the mRNA, as the cell will not translate an double-stranded mRNA. Antisense nucleic acids used in the invention are typically at least 10–12 nucleotides in length, for example, at least 15, 20, 25, 50, 75, or 100 nucleotides in length. The antisense nucleic acid can also be as long as the target nucleic acid with which it is intended that it form an inhibitory duplex. As is described further below, the antisense nucleic acids can be introduced into cells as antisense oligonucleotides, or can be produced in a cell in which a nucleic acid encoding the antisense nucleic acid has been introduced by, for example, using gene therapy methods.

In addition to blocking mRNA translation, oligonucleotides, such as antisense oligonucleotides, can be used in methods to stall transcription, such as the triplex method. In this method, an oligonucleotide winds around double-helical DNA in a sequence-specific manner, forming a three-stranded helix, which blocks transcription from the targeted gene. These triplex compounds can be designed to recognize a unique site on a chosen gene (Maher, et al., *Antisense Res. and Dev.*, 1(3):227, 1991; Helene, *Anticancer Drug Design*, 6(6):569, 1991). Specifically targeted ribozymes can also be used in therapeutic methods directed at decreasing CXCR4 expression.

Introduction of CXCR4 antisense nucleic acids into cells affected by a proliferative disorder, for the purpose of gene therapy, can be achieved using a recombinant expression vector, such as a chimeric virus or a colloidal dispersion system, such as a targeted liposome. Those of skill in this art know or can easily ascertain the appropriate route and means for introduction of sense or antisense CXCR4 nucleic acids, without resort to undue experimentation.

HOMOZYGOUS AND HETEROZYGOUS MUTATIONS IN CXCR4

It is known that in some cases, a homozygous or heterozygous mutation in a polypeptide or a regulatory region of a gene confers a molecular basis for a difference in function. Bertina, et al. and Greengard, et al. (Bertina, et al., *Nature*, 369:64, 1994; Greengard, et al., *Lancet*, 343:1361, 1994), first identified the molecular basis for the FV abnormality. The phenotype of APC resistance was shown to be associated with heterozygosity or homozygosity for a single point mutation in the FV gene that resulted in the substitution of arginine at amino acid residue 506 with glutamine (FV R506Q). This R506Q mutation prevents APC from cleaving a peptide bond at Arg-506 in FV that is required to inactivate factor Va (Bertina, supra; Sun, et al., *Blood*, 83:3120, 1994).

Similarly, the present invention envisions diagnostic and prognostic, and in addition, therapeutic approaches to treatment of HIV-associated syndromes based on homozygosity or heterozygosity of CXCR4 mutants. For example, while not wanting to be bound by a particular theory, it is believed that a subject having a homozygous mutant of CXCR4 may be HIV resistant or exhibit a slower rate of disease progression. Along the same lines, a subject having a heterozygous mutation in CXCR4 may exhibit a slower rate of disease progression than a patient having a wild type CXCR4. Mutations included in the CXCR4 coding region may also result in inactivating mutations. In addition, a mutation in the regulatory region of CXCR4 gene may prevent or inhibit expression of CXCR4, thereby providing resistance to some degree from HIV infection.

Once an individual having a homozygous or heterozygous mutant in CXCR4 is identified, it is envisioned that cells from that individual, once matched for histocompatibility, can be transplanted to an HIV positive individual, or to an "at risk" individual.

Without further elaboration, it is believed that one skilled in the art can, using the preceding description, utilize the present invention to its fullest extent. The following examples are illustrative only, and not limiting of the remainder of the disclosure in any way whatsoever.

Example 1. Characterization of CXCR4 Protein

Based on the known topology of 7-transmembrane segment proteins, four regions of CXCR4 are predicted to be exposed at the cell surface. Synthetic peptides are synthesized by methods well-known in the art that correspond to each of these 4 regions. Rabbit antisera is raised by immunization with peptide-KLH (keyhole limpet hemocyanin) conjugates. Total immunoglobulin is purified from the preimmune and the immune sera by chromatographic separation with Protein-A Sepharose.

Antibodies raised against the 38 amino acid N-terminal portion of CXCR4 blocked membrane fusion between the env-positive, LAV isolate of HIV-1, and CD4-positive, primary T cells. In contrast, antibodies raised against other peptide-KLH conjugates had no effect of membrane fusion between the virus and the target cells.

Example 2. CXCR4-Mediated Inhibition of Viral Fusion

Figure 2A:
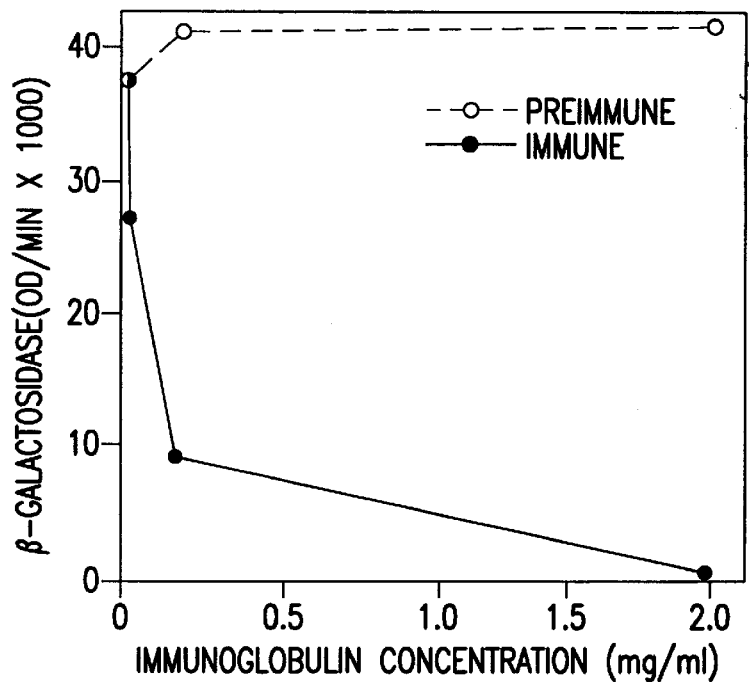
FIG. 2a depicts the inhibition of env/CD4-mediated cell fusion (as measured by β-galactosidase production) by varying concentrations of antibody against CXCR4 when reacted with the prototypic T cell line-tropic LAV strain.
Figure 2B:
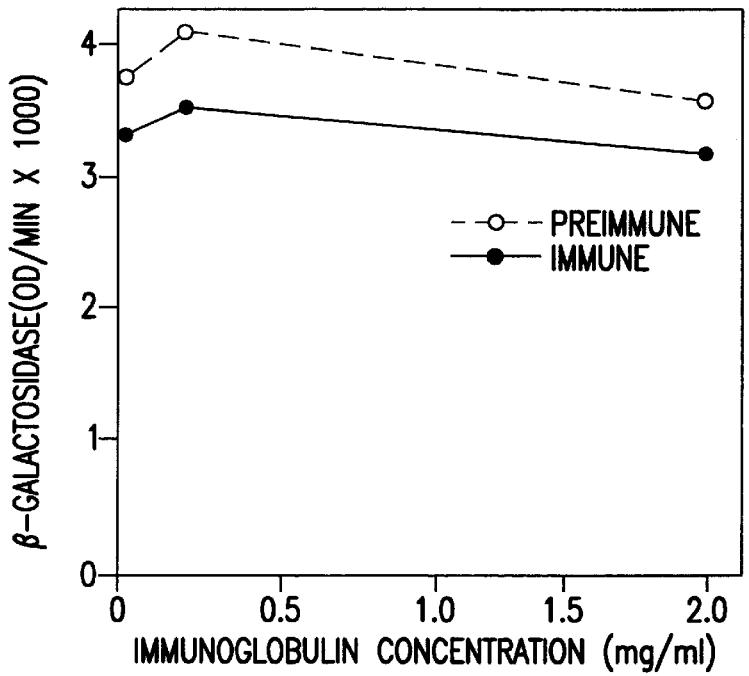
FIG. 2b depicts the inhibition of env/CD4 mediated fusion (as measured by β-galactosidase production) by varying concentrations of antibody against CXCR4 when reacted with the prototypic macrophage tropic Ba-L strain.

The sensitivity of fusion mediate by env from different HIV isolates was tested using antibodies against the N-terminal portion of CXCR4. FIGS. 2*a* and 2*b* shows that these anti-CXCR4 antibodies inhibited fusion mediated by the prototypic T cell line-tropic LAV env, but did not inhibit fusion mediated by the prototypic macrophage-tropic Ba-L env. These results indicate that the fusion inhibition with anti-CXCR4 antibodies is not due to nonspecific inhibitory effects on the cells. Table 3 demonstrates that coexpression of CXCR4 enhanced fusion much more with env from T cell line-tropic isolates (IIIB, LAV, and RF) as compared with env from macrophage-tropic strains (Ba-L, SF162, JR-FL, and ADA).

Although the invention has been described with reference to the presently preferred embodiment, it should be understood that various modifications can be made without departing from the spirit of the invention. Accordingly, the invention is limited only by the following claims.

TABLE 1

Functional Analysis of the Accessory Factor by the Vaccinia Cell Fusion Assay.
Cell mixtures were incubated as described in Text. Results indicate relative β-gal activity (OD/min x 1000) or syncytiascore (scale of 0 to +4). Where indicated, the env-expressing cells were preincubated with MAb D47 for 1 hr at room temp prior to cell mixing.

| Vac-encoded proteins on | | | Vac-encoded env on LacZ gene-containing cell | | | |
|---|---|---|---|---|---|---|
| T7 RNA Pol-expressing cell | | | Anti-V3 | WT | Unc | WT | Unc |
| Cell Type | CD4 | CXCR4 | MAb | β-gal | | syncytia | |
| NIH/3T3 | + | + | − | 1276 | 9 | +4 | 0 |
| NIH/3T3 | + | − | − | 17 | 13 | 0 | 0 |
| NIH/3T3 | − | + | − | 25 | 20 | 0 | 0 |
| NIH/3T3 | + | + | + | 148 | 9 | +1 | 0 |
| HeLa | + | + | − | 1459 | 11 | +4 | 0 |
| HeLa | + | − | − | 1311 | 10 | +4 | 0 |
| HeLa | − | + | − | 21 | 18 | 0 | 0 |
| HeLa | + | + | + | 465 | 10 | +1 | 0 |

TABLE 2

CXCR4 confers fusion competence to diverse cell types.
The indicated cell types with the known designated fusion phenotypes were cotransfected with pG1NT7β-gal (containing the LacZ gene cassette) and either control plamid pSC59 (−) or CXCR4-encoding plasmid pP$_{vac}$-CXCR4 (+); the cells were also infected with vCB3 encoding CD4. A second population of cells expressed vaccinia-encoded T7 RNA polymerase and HIV-1 env (WT or Unc). Cell mixtures were incubated at 37° C. for 3 hr. Results indicate relative

| CD4 Cell (+LacZ gene) | | Fusion Phenotype | Recombinant Expression | Env Expresssed (+T7 Pol) | |
|---|---|---|---|---|---|
| Cell Type | Species | | | WT | Unc |
| NIH/3T3 | murine | − | − | 1 | |
| | | | + | 49 | 1 |
| BS-C-1 | AGM | − | − | 1 | |
| | | | + | 60 | 1 |
| MV 1 Lu | mink | − | − | 2 | |
| | | | + | 286 | 2 |
| U-87 MG | human | − | − | 1 | |
| | | | + | 68 | 1 |
| SCL1 | human | − | − | 0 | |
| | | | + | 17 | 0 |
| HeLa | human | + | − | 127 | |
| | | | + | 187 | 1 |

TABLE 3

CXCR4 functions preferentially for envs from T-cell line tropic HIV-1 isolates.
The population of NIH/3T3 cells expressed vaccinia-encoded T7 RNA polymerase plus the replicated HIV-1 env. A second population of NIH/3T3 cells were transfected with either vac −CXCR4 (+CXCR4) or pSC59 (−CXCR4) and coinfected with vCB3 encoding CD4 plus vCBR containing the $P_{T7}$-LacZ cassette. Cell mixtures were incubated at 37° C. for 3 hr. Results indicate relative β-gal activity (OD/min × 1000).

| Env-expressing cell (+T7 pol) | | CD4-expressing cell (+LacZ gene) | |
|---|---|---|---|
| Env | Tropism of isolate | +CXCR4 | −CXCR4 |
| IIIB | T-cell line | 194 | 14 |
| LAV | T-cell line | 113 | 16 |
| RF | T-cell line | 126 | 13 |
| Ba-L | macrophage | 10 | 13 |
| SF-162 | macrophage | 14 | 15 |
| JR-FL | macrophage | 12 | 14 |
| ADA | macrophage | 37 | 19 |
| Unc (III) | nonfusogenic mutant | 12 | 13 |

What is claimed is:

1. An isolated recombinant animal host cell transformed with a polynucleotide encoding human fusion accessory factor CXCR4 polypeptide, wherein the polynucleotide is operably linked to a promoter, wherein the cell co-expresses human CXCR4 and human CD4 polypeptide, and wherein the cell is susceptible to HIV infection.

2. An isolated recombinant animal host cell transformed with a polynucleotide encoding human fiusion accessory factor CXCR4 polypeptide and a polynucleotide encoding human CD4 polypeptide, wherein the polynucleotides are operably linked to a promoter, wherein the cell co-expresses human CXCR4 and human CD4 polypeptide, and wherein the cell is susceptible to HIV infection.

3. The cell as in any of claims 1 or 2, wherein the cell is a human cell.

4. The cell as in any of claims 1 or 2, wherein the cell is a non-human primate cell.

5. The cell as in any of claims 1 or 2, wherein the cell is a mouse cell.

6. The cell as in any of claims 1 or 2, wherein the cell is a rabbit cell.

7. The cell as in any of claims 1 or 2, wherein the cell is a mink cell.

* * * * *